United States Patent [19]

Hakim et al.

[11] Patent Number: 4,551,128
[45] Date of Patent: Nov. 5, 1985

[54] CEREBROSPINAL FLUID SHUNT VALVE

[76] Inventors: Salomon Hakim, Carrera 13, N. 48-26, Bogota, Colombia; Carlos A. Hakim, 3400 Galt Ocean Dr., Apt. 1702 S., Fort Lauderdale, Fla. 33308

[21] Appl. No.: 493,748

[22] Filed: May 11, 1983

[51] Int. Cl.$^4$ ............................................. A61M 27/00
[52] U.S. Cl. ........................................ 604/9; 137/508
[58] Field of Search ....... 137/508; 128/350, DIG. 25; 604/8–10, 247

[56] References Cited

U.S. PATENT DOCUMENTS

| | | | |
|---|---|---|---|
| 2,859,770 | 11/1958 | Buivid | 137/508 |
| 3,450,155 | 6/1969 | Froehner et al. | 137/508 |
| 3,886,948 | 6/1975 | Hakim | 604/9 |
| 4,106,510 | 8/1978 | Hakim et al. | 128/350 V |
| 4,256,093 | 3/1981 | Helms et al. | 128/DIG. 25 |
| 4,332,255 | 6/1982 | Hakim et al. | 604/9 |

OTHER PUBLICATIONS

Hakim et al., "A Critical Analysis of Valve Shunts Used in the Treatment of Hydrocephalus", *Developmental Medicine and Child Neurology*, vol. 15, No. 2, Apr. 1973, pp. 230–255.
Hakim, "Hydraulic and Mechanical Mis-matching of Valve Shunts Used in the Treatment of Hydrocephalus: the Need for a Servo-Valve Shunt", *Developmental Medicine and Child Neurology*, vol. 15, No. 5, Oct. 1973, pp. 646–653.

Primary Examiner—C. Fred Rosenbaum
Assistant Examiner—Karen Kaechele
Attorney, Agent, or Firm—G. Roger Lee

[57] ABSTRACT

A surgically-implantable shunt valve for venting cerebrospinal fluid in the treatment of hydrocephalus and for shunting other body fluids, the valve having a flexible diaphragm mounted within a non-metallic housing, a plate mounted on the flexible diaphragm, the plate having a circular aperture and the diaphragm having an opening aligned with the aperture, the diaphragm being generally coplanar with the plate, the diaphragm and plate dividing the housing into inlet and outlet chambers that communicate through the aperture, the inlet and outlet chambers being generally free of blind cavities so as to inhibit collection of debris, the valve having a valve element (such as a spherical ball) residing on the inlet side of the aperture, the valve element being biased against the circular periphery of the aperture to keep it closed until the cerebrospinal fluid pressure in the inlet chamber exceeds a preselected popping pressure, and the valve having a screw for making external adjustments to the popping pressure.

31 Claims, 6 Drawing Figures

CEREBROSPINAL FLUID SHUNT VALVE

BACKGROUND OF THE INVENTION

This invention relates to shunt valves for venting cerebrospinal fluid ("CSF") in the treatment of hydrocephalus and similar conditions of impaired circulation and absorption of body fluids.

Cerebrospinal fluid shunt valves have been in use for over twenty years. Broadly speaking, they function by venting excess cerebrospinal fluid from the brain into the venous system or other receptive cavities (e.g., peritoneal, pleural). Many such valves, including the earliest designs, operate by controlling the amount of fluid flow. The neurosurgeon makes an estimate of the amount of flow required to relieve the hydrocephalus and selects a valve of that flow capacity. The selection is made difficult by the wide variation in normal flow rates.

About twenty years ago, applicant Salomon Hakim developed an altogether different valve, one that controlled intraventricular pressure rather than flow. That valve, which is today known as the Cordis-Hakim shunt valve, and which is described in U.S. Pat. No. 3,288,142, has been enormously successful and remains, even today, one of the most popular shunt valves in use. It has a spherical sapphire ball biased against a conical valve seat by a stainless steel spring. The pressure of cerebrospinal fluid pushes against the sapphire ball and spring in a direction tending to raise the ball from the seat. When the pressure difference across the valve (e.g., the pressure difference between the cerebral ventricle and the drainage site) exceeds a so-called popping pressure, the ball rises from the seat to vent cerebrospinal fluid. As the flow rate through the valve increases, the ball moves further away from the seat to provide a larger valve orifice, one that is always large enough that the pressure drop across the orifice never rises much above the popping pressure. Accordingly, the differential pressure across the valve remains nearly constant for any flow rate encountered within the cerebrospinal fluid system.

As successful as the Cordis-Hakim valve has been, it has one important limitation. It can only provide a fixed popping pressure. In treating hydrocephalus, it is often desirable to vary the popping pressure in accordance with ventricle size and treatment objective. For example, initial treatment may require a lower than normal pressure to initiate shrinkage of the ventricles, but as the ventricles decrease in size, the popping pressure should be increased gradually so that when the ventricles return to normal size the intraventricular pressure is at its normal value and the intracranial force systems are in balance (i.e., the popping pressure is set at a level that will stabilize the ventricles at a desired size). Generally speaking, the popping pressure should be varied inversely with variation in ventricle size. There is a danger, if a low pressure valve is left in a patient, of the ventricles collapsing to a condition known as "slit" ventricles. A fuller discussion of these matters can be found in Hakim et al., "A Critical Analysis of Valve Shunts Used in the Treatment of Hydrocephalus", *Developmental Medicine and Child Neurology*, Vol. 15, No. 2, Apr. 1973, pp. 230–255.

A further reason for providing adjustability in popping pressure is to correct for the wide variation in nominal popping pressure typical in manufactured valves. For example, a valve with a nominal popping pressure of 100 mm may have a much larger actual pressure. Even if that variation is discovered prior to surgery, there is nothing that can be done to correct the difficulty except to replace the valve with another, if one is available.

Pressure adjustment also has advantages in the manufacture of shunt valves. Popping pressure can be set more accurately after assembly and prior to shipment.

This adjustment capability could theoretically be achieved by modifying the original Hakim valve as shown in FIG. 5 of Hakim, "Hydraulic and Mechanical Mis-matching of Valve Shunts Used in the Treatment of Hydrocephalus: the Need for a Servo-valve Shunt", *Developmental Medicine and Child Neurology*, Vol. 15, No. 5, Oct. 1973, pp. 646–653, but the modified valve is not practical.

SUMMARY OF THE INVENTION

We have found a simple and very effective way to provide pressure adjustment in a cerebrospinal fluid shunt valve. In general the invention features a shunt valve in which a plate with a circular valve seat is supported by a diaphragm from the walls of a housing and is biased against a spherical ball (e.g., sapphire) and in which a screw is provided for making external adjustments to the popping pressure. In preferred embodiments, the screw adjusts the bias of the ball against the valve seat; the screw is mounted in the housing and either exposed externally for adjustment by an instrument piercing the skin or magnetic adjustment means are provided; the screw acts to move the ball toward the diaphragm; the ball is adhesively secured to the housing or another element of the valve and is incapable of movement absent movement of the screw; the screw extends into either the inlet or outlet chamber; the housing has two halves between which the diaphragm is clamped; two shunt valves are connected in series to provide a pumping chamber therebetween; the diaphragm, plate and housing of the valve are generally circular; the diaphragm is silicone rubber; the plate is stainless steel or sapphire; the ball is a highly-polished hard material such as sapphire; the plate is less than one half the thickness of the ball; a metallic spring is provided in the outlet chamber for biasing the plate against the ball; the spring is either a cantilever extending from one wall of the housing or a helical compression spring mounted between the plate and the housing; the adjustment screw compresses one end of the helical spring or bears against a portion of the cantilever spring. In other preferred embodiments, popping pressure adjustment is provided by adjusting the amount of travel allowed for the ball, after which the ball but not the plate is prevented from moving further; a post whose height is adjusted by turning a screw is used to adjust the point at which ball travel is stopped and the valve opens; and a cage extending over the ball and secured to the plate at either side thereof prevents the ball from leaving the vicinity of the valve seat (but allows the ball to spin for self-cleaning).

The invention provides a simple, practical to manufacture, highly reliable, and compact shunt valve with pressure adjustment capability. Popping pressure can be easily and accurately set at the factory, during or prior to surgery, and after implantation, either by a screwdriver-like instrument or by application of a magnetic field. In addition, the valve has reduced opaqueness to X-rays (and thus reduced interference with CAT scanning equipment), little or no susceptibility to interference from NMR equipment, and low susceptibility to clogging with debris.

Other advantages and features of the invention will be apparent from the following description of the preferred embodiments and from the claims.

DESCRIPTION OF THE PREFERRED EMBODIMENTS

Figure 1:
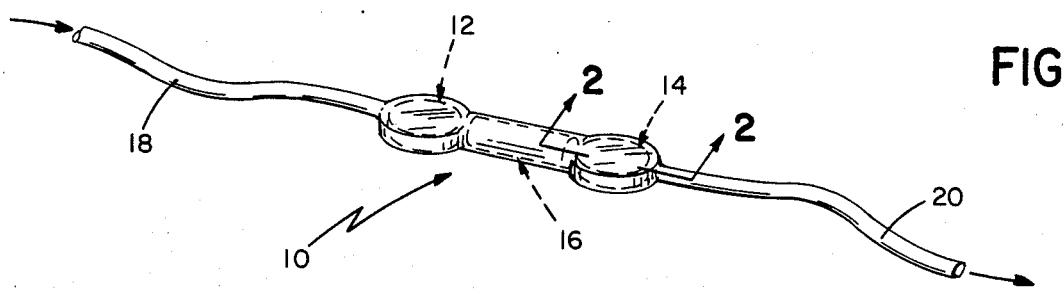
FIG. 1 is a perspective, somewhat diagrammatic, view of a first preferred embodiment of the invention.

There is shown in FIG. 1 a shunt valve assembly 10 with two shunt valves 12, 14 separated by a pumping chamber 16. Cerebroventricular catheter 18 is connected to the inlet of the valve assembly, and drainage catheter 20, to the outlet. This assembly can be surgically implanted following well-known procedures.

Figure 2:
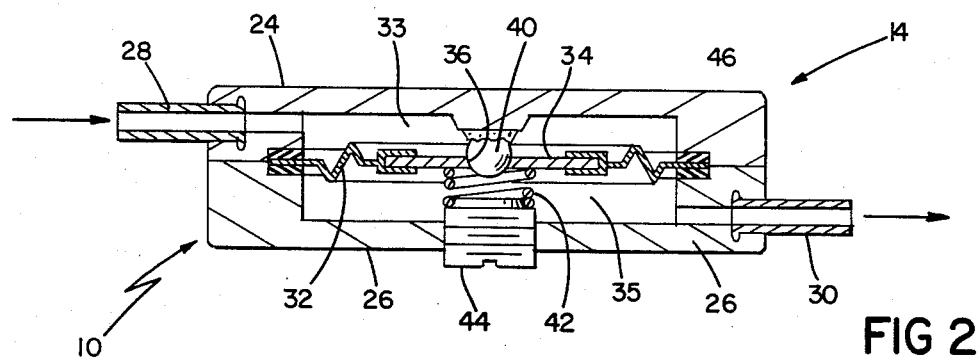
FIG. 2 is a cross-sectional view taken along 2—2 in FIG. 1 showing the internal construction of the shunt valves of said embodiment.

There is shown in FIG. 2 a cross section of the shunt valve 14. (Shunt valve 12 is similar to valve 14 except that it lacks the pressure adjustment capability.) The valve body (injection molded polyethersulfone plastic) consists of two halves 24, 26 with stainless steel inserts forming an inlet tube 28 and an outlet tube 30. Supported between the two halves is diaphragm 32 (silicone rubber), which has secured (captured in an annular groove) to its center a circular plate 34 (stainless steel). The diaphragm and plate divide the housing interior into inlet chamber 33 and outlet chamber 35. Formed in the middle of the metal disk is a circular aperture 36, the periphery of which forms a valve seat for spherical ball 40 (highly-polished sapphire). The ball is adhered (by conventional adhesive) to the upper interior surface of inlet chamber 33 (or it could be press fit inside a socket). The circular valve seat has a coined, beveled edge. (Plate 34 could also be sapphire, just as ball 40, in which case other conventional techniques would be used to form the beveled edge.) A helical compression spring 42 (stainless steel) is provided to bias plate 34 against ball 40. The spring is installed between the plate and an adjustment screw 44 (self lubricating plastic such as polyethylene) threaded through lower half 26 of the housing. Metal rings 46 (stainless steel) clamp the periphery of diaphragm 32 between halves 24, 26 of the housing. Adjustment is made to the popping pressure by rotating screw 44 so as to vary the spring preload of the plate against the ball. It is preferred that the bias force of plate 34 against ball 40 be provided for the most part by metal spring 42 rather than by diaphragm 32, because any force provided by the diaphragm, which is an elastomer, will change over the life of the valve.

Figure 3:
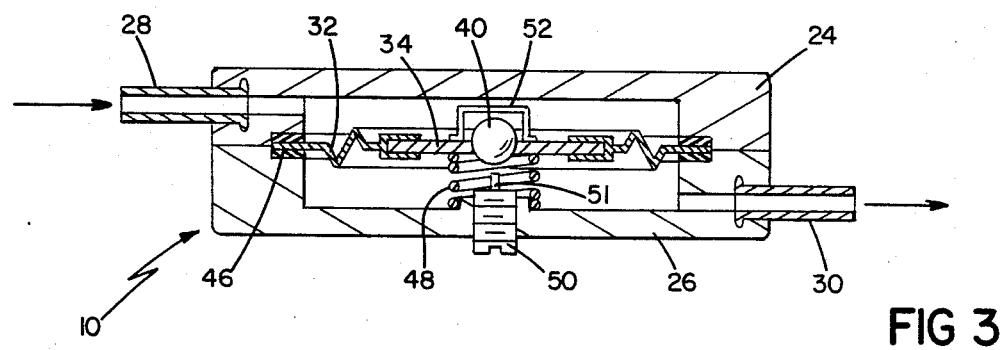
FIG. 3 is a cross-sectional view of a second preferred embodiment (taken along the same section as FIG. 2).

There is shown in FIG. 3 another preferred embodiment similar to that of FIG. 2 except that the base of helical spring 42 is not supported on the adjustment screw but rather rests directly on the housing. Adjustment screw 50 has ball support post 51 at its upper end. Ball 40 is prevented from leaving the vicinity of the valve seat by wire 52 (welded at either side of the ball to plate 34), which acts like a cage for the ball. In operation the ball and plate move downward together, and the valve remains sealed, until ball 40 strikes the top of post 51. Thereafter the ball is prevented from moving any further downward, and the valve opens. The popping pressure is, therefore, dependent upon the pressure required to move the plate and ball downward to where the ball strikes the post. Thus it is possible to adjust the popping pressure merely by rotating screw 50 to adjust the height of the post. An advantage of this embodiment is that the ball is free to move (e.g., spin) and thus to avoid build up of debris in its vicinity.

Figure 4:
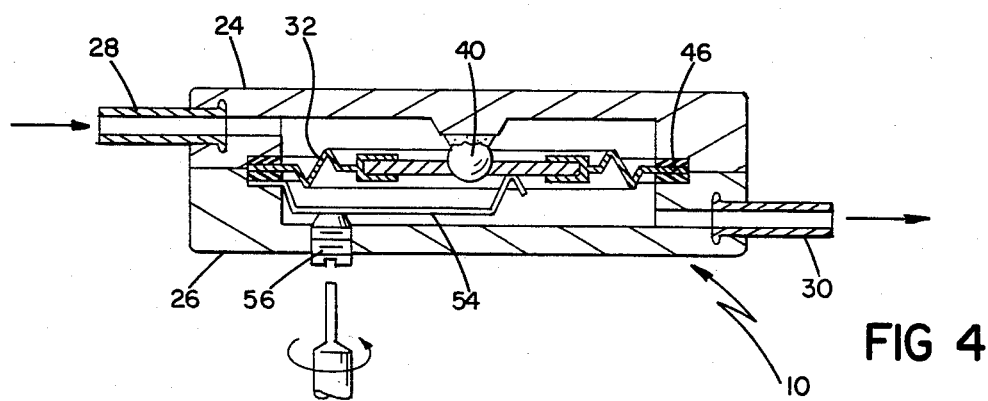
FIG. 4 is a cross-sectional view of a third preferred embodiment (taken along the same section as FIG. 2).

There is shown in FIG. 4 another preferred embodiment in which ball 40 is fixed in place as in the embodiment of FIG. 2 but in which a cantilever spring 54 replaces the helical spring. Adjustment of the bias of ball 40 against the valve seat is accomplished by adjustment screw 56 extending into the outlet chamber and contacting cantilever spring 54 intermediate its base (where it is welded to ring 46) and its free end (where it contacts the underside of plate 34).

Figure 5:
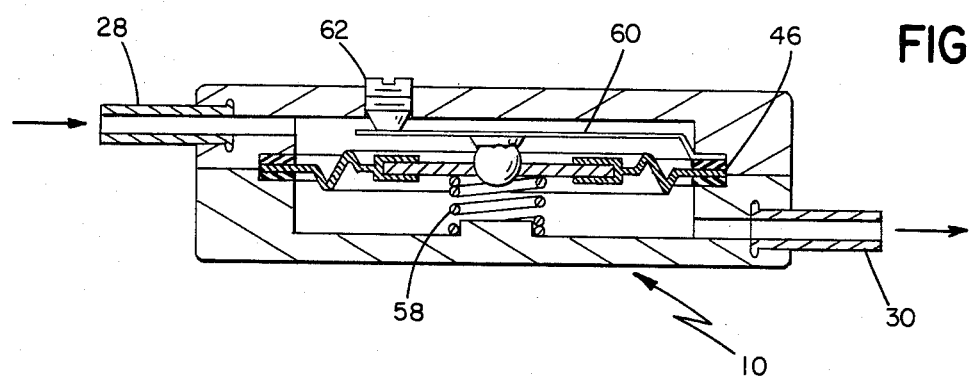
FIG. 5 is a cross-sectional view of a fourth preferred embodiment (taken along the same section as FIG. 2).

There is shown in FIG. 5 another preferred embodiment in which there is provided in the outlet chamber a helical compression spring 58 similar to spring 48 in FIG. 3. Ball 40 is adhesively secured to a cantilever arm 60 welded to the upper metal ring 46. Bias adjustment of the ball against the valve seat is made using adjustment screw 62, which extends into the inlet chamber and contacts the free end of cantilever spring 60.

Figure 6:
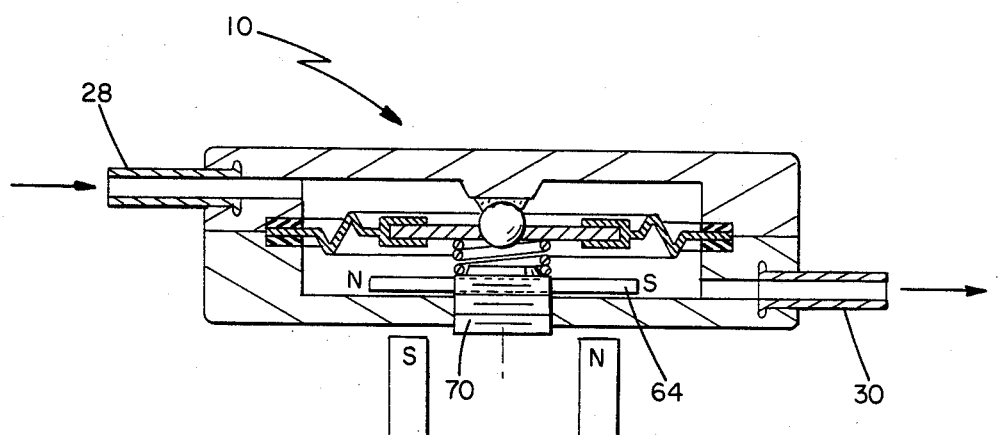
FIG. 6 is a cross-sectional view of a fifth preferred embodiment (taken along the same section as FIG. 2) in which a magnet is provided to permit noninvasive valve adjustments to be made.
Figure 6:
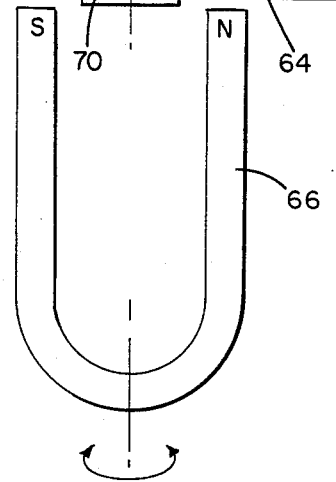

There is shown in FIG. 6 another preferred embodiment which is similar to that shown in FIG. 2 except that a magnet 64 has been attached to adjustment screw 44 (by mounting through a hole in the screw) to permit noninvasive magnetic adjustment of the popping pressure after surgical implantation. The magnet is installed so that the line connecting the poles is normal to the axis of rotation of the screw. That permits the screw to be turned by placing another magnet 66 in the orientation suggested in FIG. 6 and then turning the external magnetic around an axis generally parallel to the axis of screw rotation. The use of an external magnetic field to adjust a cerebrospinal fluid shunt valve is described in Hakim, "Hydraulic and Mechanical Mis-matching of Valve Shunts Used in the Treatment of Hydrocephalus: the Need for a Servo-valve Shunt", *Developmental Medicine and Child Neurology*, Vol. 15, No. 5, Oct. 1973, pp. 646–653.

Other Embodiments

Other embodiments are within the scope of the following claims. For example, the ball could be moved by the adjustment screw in ways other than the example shown in FIG. 5, and other means than the cantilever spring of FIG. 4 and the helical springs of FIGS. 2, 3, 5 and 6 could be used to provide the spring bias of the ball against the valve seat.

What is claimed is:

1. A surgically-implantable shunt valve for venting cerebrospinal fluid in the treatment of hydrocephalus and for shunting other body fluids, said valve comprising
   a housing constructed of a surgically-implantable, non-metallic material,
   a diaphragm support consisting of a single flexible diaphragm mounted within said housing, a plate mounted on said flexible diaphragm, said plate being provided with a circular aperture and said diaphragm having an opening aligned with said aperture.

said diaphragm being generally coplanar with said plate, said diaphragm and plate dividing said housing into an inlet and an outlet chamber that communicate through said aperture, said inlet and outlet chambers being generally free of blind cavities so as to inhibit collection of debris, a valve element of diameter larger than said aperture, said valve element residing on the inlet side of said aperture, means for biasing said valve element signal the circular periphery of said aperture so as to keep said aperture closed until the cerebrospinal fluid pressure in said inlet chamber exceeds a preselected popping pressure and so as to open said aperture when said popping pressure is exceeded so as to vent cerebrospinal fluid through said aperture into said outlet chamber, said popping pressure being on the order of cerebrospinal fluid pressures (i.e, less than 300 mm $H_2O$,)

said housing including inlet and outlet ports communicating with said inlet and outlet chambers respectively for connecting said inlet and outlet chambers to external catheters or other fluid conduits, and screw means for making external adjustments to said preselected popping pressure.

2. The shunt valve of claim 1 wherein said screw means includes means for making adjustments to the bias of said valve element against said circular periphery of said aperture.

3. The shunt valve of claim 1 wherein said screw means comprises a screw mounted in said housing.

4. The shunt valve of claim 3 wherein one end of said screw is exposed outside of said housing to provide for external adjustment.

5. The shunt valve of claim 4 wherein said exposed end is adapted to be adjusted by an instrument piercing the skin to make said adjustments.

6. The shunt valve of claim 1 wherein there is further provided valve element movement means for moving said ball in a direction normal to said plate and wherein said screw means includes means cooperating with said valve element movement means for moving said valve element by means of said external adjustments.

7. The shunt valve of claim 6 wherein said screw extends into said inlet chamber.

8. The shunt valve of claim 1 wherein said valve element is adhesively secured to said housing or other element of said valve.

9. The shunt valve of claim 8 wherein said ball is secured so that absent an adjustment of said screw means all movement of said valve element is prevented.

10. The shunt valve of claim 1 wherein said screw means further comprises magnetic adjustment means comprising a magnetic element mounted within or on said valve in such a way as to perform popping pressure adjustment when subjected to an external magnetic field.

11. The shunt valve of claim 10 wherein said screw means comprises a screw mounted in said housing and said magnetic element is a magnet mounted so that the line connecting the two poles of said magnet is transverse to the axis of rotation of said screw all so that said screw can be turned by applying an external magnetic field that rotates about an axis generally parallel to the axis of rotation of said screw.

12. The shunt valve of claim 1 wherein said housing comprises two halves joined at mating faces and the periphery of said diaphragm is clamped between said two halves in the vicinity of said mating faces.

13. The shunt valve of claim 1 connected in series downstream of a second shunt valve and with ventricular and drainage catheters, said first-mentioned and second shunt valves being connected via a conduit adapted to be manually squeezed to effect a pumping action through the two valves, the inlet of said first-mentioned valve being connected to one end of the conduit and the outlet of said second valve being connected to the other end of said conduit, said ventricular catheter being connected to the inlet of said second valve and said drainage catheter being connected to the outlet of said first-mentioned valve, and said second valve being of the same construction as said first-mentioned valve except that said screw means for adjusting the popping pressure may be absent.

14. The shunt valve of claim 1 wherein said diaphragm and housing are generally circular in shape when viewed along a direction normal to said plate and aperture.

15. The shunt valve of claim 14 wherein said plate is circular and is mounted at the center of said circular diaphragm.

16. The shunt valve of claim 15 wherein said diaphragm is silicone rubber, said plate is stainless steel or sapphire, said valve element is a highly-polished, hard material such as sapphire, and said housing is injection molded using a surgically-implantable plastic such as polyethersulfone.

17. The shunt valve of claim 1 wherein the thickness of said plate is less than half the diameter of said valve element.

18. The shunt valve of claim 1 wherein said means for biasing comprises a metallic spring in said outlet chamber for providing a force upon said metal plate in such a direction as to bias said plate against said valve element.

19. The shunt valve of claim 18 wherein said metallic spring is a cantilever supported from said housing at the periphery of said outlet chamber.

20. The shunt valve of claim 19 wherein the free end of said cantilever spring bears against said plate or against a surface of said diaphragm directly beneath said plate.

21. The shunt valve of claim 18 wherein said metallic spring comprises a helical compression spring extending generally normally to said plate and aligned with said aperture.

22. The shunt valve of claim 21 wherein said screw means provides a compressive force on one end of said helical spring and the other end bears on portions of said plate surrounding said aperture.

23. The shunt valve of claim 22 wherein said screw means comprises a screw extending into said outlet chamber and bearing on one end of said helical spring.

24. The shunt valve of claim 19 wherein said screw means comprises a screw extending into said outlet chamber and bearing on said cantilever spring intermediate its two ends so as to provide adjustment of the force applied by said spring to said plate.

25. The shunt valve of claim 8 wherein said valve element is secured to an arm extending from the housing and wherein said screw means is adapted to move said arm toward and away from said plate to provide adjustment of said bias.

26. The shunt valve of claim 25 wherein said arm is a metallic cantilever spring and the base of said arm is secured to said housing at the periphery of said inlet chamber.

27. The shunt valve of claim 26 wherein said screw means comprises a screw extending into said inlet chamber and contacting said arm and wherein said valve element is adhesively secured to said arm intermediate said screw contact and arm base.

28. The shunt valve of claim 1 wherein said valve element is a spherical ball and wherein said screw means comprises a ball support means for stopping travel of said ball but not said plate, thereby causing said valve to open, when said popping pressure is reached.

29. The shunt valve of claim 28 wherein said ball support means comprises a post attached to said screw means and vertically adjustable so that the top of said post strikes said ball at said popping pressure.

30. The shunt valve of claim 1 wherein said screw extends into said outlet chamber.

31. The shunt valve of claim 29 wherein said ball is held in place by cage means extending over said ball and secured at either side thereof to said plate.

* * * * *

UNITED STATES PATENT AND TRADEMARK OFFICE
CERTIFICATE OF CORRECTION

PATENT NO. : 4,551,128
DATED : November 5, 1985
INVENTOR(S) : Salomon Hakim, Carlos A. Hakim It is certified that error appears in the above-identified patent and that said Letters Patent are hereby corrected as shown below:

Column 5, claim 1, line 16, "signal" is changed to --against--.

Signed and Sealed this

Eighth Day of April 1986

[SEAL]

Attest:

DONALD J. QUIGG

Attesting Officer

Commissioner of Patents and Trademarks